United States Patent [19]

Mouzin et al.

[11] Patent Number: 5,059,599
[45] Date of Patent: Oct. 22, 1991

[54] DERIVATIVES OF 1-PHENYL 1,4-DIHYDRO 3-AMINO 4-OXO PYRIDAZINES, THEIR PREPARATION AND THEIR USE IN THERAPY

[75] Inventors: Gilbert Mouzin, Toulouse; Henri Cousse; Jean-Francois Patoiseau, both of Castres; Jean-Marie Autin, Labruguiere; Dennis Bigg, Castres, all of France

[73] Assignee: Pierre Fabre Médicament, Paris, France

[21] Appl. No.: 534,180

[22] Filed: Jun. 6, 1990

[30] Foreign Application Priority Data

Jun. 7, 1989 [FR] France ............................. 89 07532

[51] Int. Cl.$^5$ .......................................... C07D 237/22
[52] U.S. Cl. ................... 514/247; 514/236.5; 514/252; 544/114; 544/238; 544/239
[58] Field of Search .................. 544/239, 238, 114; 514/247, 252, 236.5

[56] References Cited

U.S. PATENT DOCUMENTS

| 2,798,869 | 7/1957 | Druey et al. | 544/239 |
| 4,238,490 | 12/1980 | Powers et al. | 544/240 |
| 4,561,881 | 12/1985 | Labovitz et al. | 544/238 |
| 4,661,145 | 4/1987 | Fujimoto | 544/239 |
| 4,672,063 | 6/1987 | Jasserand et al. | 514/252 |

FOREIGN PATENT DOCUMENTS 7806494 10/1978 France .

OTHER PUBLICATIONS

Staehelin et al., Chem. Abstr. vol. 51, entry 4380dt (1957).
S. Plescia et al., J. Heterocyclic. Chem. 18, 333–334 (1981).
A. Staehelin et al., Helv. Chim. Acta 39, 1741–1754 (1956).

Primary Examiner—Donald G. Daus
Attorney, Agent, or Firm—Gordon W. Hueschen

[57] ABSTRACT

The present invention relates to derivatives of 1-phenyl 1,4-dihydro 3-amino 4-oxo pyridazines of the general formula I:

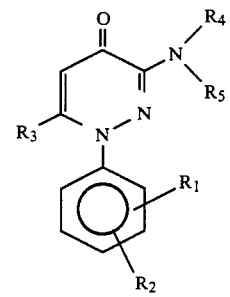

and the production thereof.

It also concerns pharmaceutical compositions comprising as active principle a compound of general formula I and use thereof for treatment of central nervous system disturbances, especially as an anxiolytic.

9 Claims, No Drawings

DERIVATIVES OF 1-PHENYL 1,4-DIHYDRO 3-AMINO 4-OXO PYRIDAZINES, THEIR PREPARATION AND THEIR USE IN THERAPY

The present invention, developed at the Pierre Fabre Medicament Research Center, has as its object new chemical compounds, their method of preparation and their use as medicines. The new chemical compounds claimed by the applicant, have general formula I:

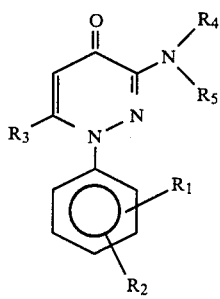

in which:

$R_1$, $R_2$ which are identical or different represent a hydrogen, a lower alkyl group or an alkyloxy group, a halogen, a trifluoromethyl radical.

$R_3$ represents a hydrogen, a branched or unbranched $C_{1-6}$ lower alkyl group or an aryl or arylalkyl group, with the exception of methyl when $R_1$, $R_2$, $R_4$ and $R_5$=H.

$R_4$ represents hydrogen, a linear or branched $C_{1-6}$ alkyl radical or a cycloalkyl radical or forms with $R_5$ and the nitrogen atom to which they are bound a heterocycle such as pyrrole, pyrrolidine, morpholine, piperidine, imidazole or piperazine, possibly substituted in 4 position.

$R_5$ represents:

hydrogen, a linear or branched $C_{1-6}$ alkyl radical, an aminoalkyl group II

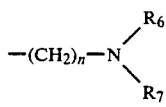

in which n is between 1 and 6 and $R_6$, $R_7$, which are identical or different, represent hydrogen or an alkyl or cycloalkyl group, or, together with the nitrogen atom to which they are bound, form a heterocycle such as piperidine, pyrrolidine, morpholine or piperazine, possibly substituted in 4 position;

a 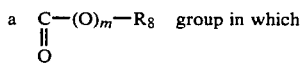 group in which m may be equal to 0 or 1 and $R_8$ represents a linear or branched $C_{1-6}$ alkyl group or an aryl or arylalkyl group or amino alkyl group II such as defined above;

- or a 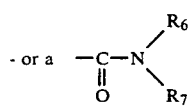

group in which $R_6$ and $R_7$ have the same meaning as above.

The invention covers the therapeutically acceptable organic or inorganic salts of these molecules.

The present invention also concerns the preparation of derivatives of formula I by a method which is characterized by the fact that it comprises:

(a) a preliminary step which consists in transforming the pyridazine carboxylic acid of formula III, or one of its activated forms, into its azide and/or its corresponding isocyanate of formula V

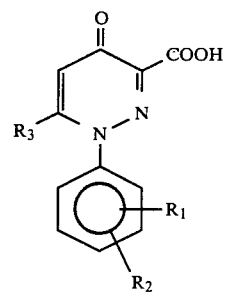

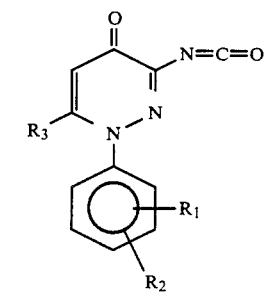

$R_1$, $R_2$, $R_3$ having the same meaning as above (b) a step which consists in transforming the compound obtained in accordance with (a) into a compound of general formula I and, if applicable, (c) a step for transforming this compound of formula I thus obtained into another compound of formula I.

In the pyridazine carboxylic acid of formula III, the radicals $R_1$, $R_2$, $R_3$ have the same meaning as previously and which can be obtained by the methods described in particular by:

S. PLESCIA et al., J. Heterocyclic. Chem. 18, 333–334 (1981)

French Patent No. 7806494 of Nov. 13, 1978

A. STAEHELIN et al., Helv. Chim. Acta 39, 1741–1754 (1956).

The acid III can be transformed into isocyanate by different methods:

a) the acid III treated with the DPPA or activated in the form of a mixed anhydride obtained by action of an alkyl chloroformate and then treated with a nitride such as Na-nitride or TMSA-azide, upon decomposition by heating in a solvent such as ethyl acetate, dioxane or toluene, gives the corresponding isocyanate.

b) The ethyl ester, obtained by the action of ethyl chloroformate in the presence of triethylamine on acid III, is transformed into primary amide by treatment with 30% ammonia in a solvent such as methanol.

The primary amide, subjected to the action of a sodium hypohalite, and more particularly, Javel (Javelle) water (aqueous sodium hypochlorite) in caustic soda in the presence of a solvent such as THF, make it possible to obtain the isocyanate.

The isocyanate, without being isolated, can be treated:

by a basic aqueous solution in order to supply the primary amine I ($R_4=R_5=H$);

by an $R_9OH$ alcohol in order to obtain the carbamate

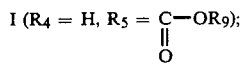

In this case, alcohol $R_9OH$ can be used as reaction solvent or cosolvent to form isocyanate and obtain carbamate:

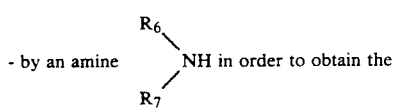

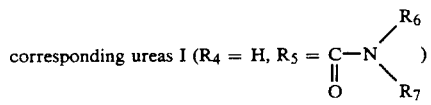

the radicals $R_6$ and $R_7$ having the same meaning as above.

The monosubstituted amines can be obtained from the primary amine I ($R_4=R_5=H$) by conventional techniques such as benzoylation, alkylation, debenzoylation. In accordance with the present invention, they can also be obtained advantageously by treatment of a carbamate by an $R_{10}X$ compound followed by basic hydrolysis, or acid hydrolysis in the case of t-butyl carbamate, $R_{10}$ representing a linear, branched or cyclic alkyl radical,

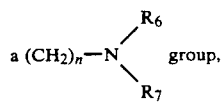

n, $R_6$ and $R_7$ having the same meaning as previously, and X representing a labile group such as a halogen.

The tertiary amines can be obtained by alkylation of the secondary amines by an $R_{10}X$ compound, $R_{10}$ and X having the same meaning as above, in the presence of an agent such as sodium hydride or caustic soda.

In accordance with the present invention, the substituted amines can also by obtained be treatment of the chlorinated derivative IV by an amine

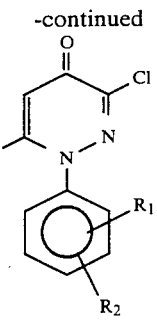

$R_1$, $R_2$, $R_3$ having the same meaning as above and $R_{11}$ representing hydrogen, a linear, branched or cyclic $C_{1-6}$ alkyl radical, or one capable of forming with $R_{12}$ and the nitrogen atom to which they are bound a heterocycle such as pyrrole, pyrrolidine, morpholine, piperidine, imidazole or piperazine, possibly substituted in 4 position.

$R_{12}$ representing a linear or branched $C_{1-6}$ alkyl radical or a

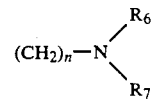

group in which $R_6$, $R_7$ and n have the same meaning as above.

The compound IV can be obtained by a reaction of the Sandmeyer type by treating the amine I ($R_4=R_5=H$) with a nitrite such as t-butyl nitrite and then the diazoic derivative formed with the anhydrous cupric chloride. This reaction is carried out in an anhydrous medium such as dimethyl formamide, in the presence of molecular sieves.

The following examples serve to illustrate the present invention, but are not to be construed as limiting.

The percentage analyses as well as the IR and NMR spectra confirm the structure of the compounds obtained.

The present invention also refers to the use of synthetic intermediates of general formula IV by way of new compounds.

It also concerns pharmaceutical compositions which are characterized by the fact that as active principle they contain at least one compound in accordance with the invention. These compounds of general formula I can furthermore be associated with another active principle in said compositions.

EXAMPLE 1

1-(m-trifluoromethylphenyl) 1,4-dihydro 4-oxo 3-amino 6-methyl pyridazine (Compound 1)

A solution of 1-(m-trifluoromethylphenyl) 1,4-dihydro 4-oxo 6-methyl pyridazine 3-carboxylic acid (29.8 g-0.1 mol) in 150 ml of acetone and 15.5 ml of triethylamine (0.11 mol) is cooled to $-15°$ C.

Without exceeding $-5°$ C., 10.5 ml of ethyl chloroformate (0.11 mol) is added drop by drop followed by agitation for 2 hours at 0° C. A solution of sodium nitride (14.6 g $-0.22$ mol) in 60 ml of water is then added. The agitation is maintained for one hour at 0° C., whereupon the acetone is evaporated under vacuum and the residue taken up in 250 ml of toluene.

After heating for 1 hour under reflux and concentration under vacuum, it is taken up by 160 ml of 8N hydrochloric acid and heated for 1 hour at 100°-110° C.

The mixture is poured onto ice, neutralized with 6N sodium hydroxide solution and extracted with ethyl acetate. After washing with water, drying and concentration, it is triturated in ethyl ether in order to obtain 19.2 g of compound 1.

Yield—71%.
MP=178°-179° C.
Thin layer chromatography: Rf=0.25 (ethyl acetate)

EXAMPLE 2

1-(m-trifluoromethylphenyl) 1,4-dihydro 4-oxo 3-amino 6-methyl pyridazine (Compound 1)

a) 1-(m-trifluoromethylphenyl) 1,4-dihydro 4-oxo 6-methyl pyridazine 3-ethylcarboxylate Ice a solution of 1-(m-trifluoromethylphenyl) 1,4-dihydro 4-oxo 6 methyl pyridazine 3-carboxylic acid (105 g-0.35 mol) in chloroform (750 ml) which contains triethylamine (58.5 ml-0.42 mol). Add ethyl chloroformate (36 ml-0.376 mol) drop by drop. After stirring for one hour at 0° C., allow to return to room temperature, wash with sodium bicarbonate, then with water and then with salt water. After drying over sodium sulphate, concentrate the organic phase in vacuum and take up in ethyl ether.

After filtration, washing and drying, 105 g of ester are obtained.

(Yield=92%)
MP=169°-170° C.
Thin layer chromatography: Rf=0.24 (ethyl acetate)

b) 1-(m-trifluoromethylphenyl) 1,4-dihydro 4-oxo 6-methyl pyridazine 3-carboxamide The ester obtained above (98.6 g-0.3 mol) is dissolved at 60° C. in methanol (750 ml). 30% ammonia (490 ml) is then added and heating is effected for one hour at 65°-70° C.

The methanol is evaporated under vacuum. After being taken up in water, filtered, washed and dried under vacuum, 87 g of carboxamide are obtained.

(Yield=96%).
MP=>250° C.
Thin layer chromatography: Rf=0.40 (MeOH-CHCl$_3$:15-85).

c) 1-(m-trifluoromethylphenyl) 1,4-dihydro 4-oxo 3-amino 6-methyl pyridazine (Compound 1)

To a suspension of 2.97 g (0.01 mol) of carboxamide obtained above, in THF (100 ml), 1N caustic soda (40 ml-0.04 mol) is added, as well as Javel water at 24° C. (15 ml). After agitation for one hour at room temperature, the initial suspension has become clear and the mixture is then brought to 60° C. for one hour. After cooling, the mixture is diluted with ethyl acetate, washed with water, and then dried, filtered and concentrated under vacuum. The residue obtained is taken up in ethyl ether, filtered and dried in order to obtain compound 1 (2.20 g).

(Yield—81%).
MP=179° C.
Thin layer chromatography: Rf=0.25 (ethyl acetate).

EXAMPLE 3

1-(m-trifluoromethylphenyl) 1,4-dihydro 3-t-butyloxycarbonylamino 4-oxo 6-methyl pyridazine (Compound 2)

a) to a suspension of 1-(m-trifluoromethylphenyl) 1,4-dihydro 4-oxo 6 methyl pyridazine 3-carboxylate (2.98 g-0.01 mol) in 20 ml of terbutanol there are added 1.54 ml (0.011 mol) of triethylamine and 2.6 ml (0.012 ml) diphenylphosphorylazide, followed by heating for 2 hours at 80° C.

b) The mixture is evaporated under vacuum and taken up in sodium bicarbonate and then extracted with ethyl acetate. After washing with water, drying over sodium sulphate and evaporation in vacuum, compound 2 is recrystallized from a 50—50 ether/hexane mixture (3.16 g)

(Yield=85%).
MP=170°-171° C.
Thin layer chromatography: Rf=0.42 (ethyl acetate)

c) The reaction mixture obtained in accordance with b) is treated with 16 ml of 6N hydrochloric acid and then heated for 30 minutes at 50° C., whereupon it is poured over 50 ml of iced 2N caustic soda.

After extraction with ethyl acetate, washing with water, drying over sodium sulphate and evaporation under vacuum, compound 1, as defined in the preceding example, crystallizes from a 10-90 ethyl-ether/hexane mixture (2.2 g)

(Yield=80%),
MP=174°-175° C.

EXAMPLE 4

1-(m-trifluoromethylphenyl) 1,4-dihydro 4-oxo 3-amino pyridazine (Compound 3)

Operating in the same manner as described in Examples 2a and 2c, compound 3 is obtained from 1-(m-trifluoromethylphenyl) 1,4-dihydro 4-oxo pyridazine 3-carboxylic acid.

MP=131° C.
Thin layer chromatography: Rf=0.3 (ethyl acetate).

EXAMPLE 5

1-(m-trifluoromethylphenyl) 1,4-dihydro 3-(3'-n-butyl)ureido 4-oxo 6-methyl pyridazine (Compound 4)

2.98 g of 1-(m-trifluoromethylphenyl) 1,4-dihydro 4-oxo 6-methyl pyridazine 3-carboxylic acid in 50 ml of ethyl acetate are treated for 2¼ hours at 60° C. in the presence of triethylamine (2.1 ml) and diphenyl phosphorylazide (3.4 ml). 2.96 g of n-butylamine and are then added, the mixture being maintained at 60° C. for 30 minutes. The reaction mixture is washed with a solution of NaHCO$_3$ and then with water, dried over Na$_2$SO$_4$ and evaporated to dryness.

After trituration in ethyl ether, the compound 4 (2.2 g) is obtained.

(Yield=60%)
MP=157° C.
Thin layer chromatography: Rf=0.7 (methanol-CHCl$_3$: 15-85).

EXAMPLE 6

1-(m-trifluoromethylphenyl) 1,4-dihydro 3-benzamido 4-oxo 6-methyl pyridazine (Compound 5)

To a solution of 8.07 g of compound 1 in ethyl acetate (180 ml), 6 ml of triethylamine are added and then, drop by drop, 4.2 ml of benzoyl chloride in 20 ml of ethyl acetate.

After agitation for 2 hours, dilution with water, decantation and then washing with water, the organic phase is dried over $Na_2SO_4$ and evaporated under vacuum.

Compound 5 (8 g) is obtained by trituration in ethyl ether and recrystallization from ethyl acetate.
(Yield=71%)
MP=186° C.
Thin layer chromatography: Rf=0.3 (ethyl acetate).

EXAMPLE 7

1-(m-trifluoromethylphenyl) 1,4-dihydro 3-methylamino 4-oxo 6-methyl pyridazine (Compound 6)

To a solution of benzamide 5 (5.48 g) in dimethylacetamide (50 ml), 337 mg of benzyl triethylammonium chloride, 5.85 ml of 10N caustic soda and 1.58 ml of methyl sulphate are added. After agitation for 1 hour at 20° C., the solution is diluted with ethyl acetate and water, decanted, washed with water and then concentrated under vacuum. It is taken up in 50 ml of 1N caustic soda and 50 ml of 95 ethanol and heated for 3 hours under reflux. After being taken up in ethyl acetate, washing with water and drying over $Na_2SC_4$, the organic phase is evaporated in vacuum and taken up by a mixture of ether and petroleum ether. Crude compound 6 is thus obtained, which can be recrystallized from ethyl acetate (2.48 g)
(Yield=59%).
MP=179° C.
Thin layer chromatography: (Rf=0.4 (methanol-$CHCl_3$: 15–85).

EXAMPLE 8

1-(m-trifluoromethylphenyl) 1,4-dihydro 3-dimethylamino 4-oxo 6-methyl pyridazine (Compound 7)

Compound 6 (3.9 g) is treated with sodium hydride (413 mg) in dimethylacetamide (20 ml) for 1 hour. 2.42 ml of methyl iodide are then added and agitated for 1 hour at 20° C. and then for 1 hour at 60° C.

The mixture is poured onto water. The crystals obtained are filtered, washed with water and then taken up with ethyl acetate. After drying, decolorizing, and evaporation, compound 7 is obtained by being taken up in an ethyl-ether/hexane mixture, and it can then be recrystallized from a 95:5 ethylether/acetone mixture (2 g—Yield=50%)
MP=150° C.
Thin layer chromatography: Rf=0.20 (ethyl acetate)

EXAMPLE 9

1-(p-chlorophenyl) 1,4-dihydro 3-methylamino 4-oxo 6-methyl pyridazine (Compound 8)

To a suspension of 1.57 g of 1-(p-chlorophenyl) 1,4-dihydro 3-(t-butyloxycarbonylamino) 4-oxo 6-methyl pyridazine obtained from the corresponding acid in accordance with Example 2a and 2b in THF (60 ml), there are added 105 mg of CBTA, 9 ml of 6N caustic soda and 1.74 ml of methyl iodide. After one night at room temperature, the reaction mixture, to which water is added, is extracted with ethyl acetate. The organic phase, dried over $Na_2SO_4$ and evaporated in vacuum, gives a thick oil (1.68 g) which is taken up in 3 ml of methanol and then 7.8 ml of 6N hydrochloric acid is added. After 2 hours at room temperature, the mixture is poured onto 8 ml of 6N caustic soda and extracted with ethyl acetate. The organic phase, dried and evaporated in vacuum, is taken up with hexane in order to precipitate compound 8 (916 mg).
(Yield=78%)
Mp=214°-215° C.
Thin layer chromatography: Rf=0.23 (ethyl acetate).

EXAMPLE 10

1-(m-trifluoromethylphenyl) 1,4-dihydro 3-chloro 4-oxo 6-methyl pyridazine (Compound 9)

To a solution of dimethylformamide maintained at 0° C. there are added, in succession, crushed molecular sieves (3 g), terbutyl nitrite (5 g), anhydrous cupric chloride (2.95 g) and, in small portions, 1-(m-trifluoromethylphenyl) 1,4-dihydro 4-oxo 3-amino 6-methyl pyridazine (Compound 1) (5 g) in solution of DMF (10 ml).

After agitation for 30 minutes at 0° C. and then for 30 minutes at 60° C. and filtration, the solution is taken up in water and extracted with ethyl acetate. After drying over $Na_2SO_4$ and evaporation in vacuum, compound 9 is obtained by trituration in ether (3.81 g).
(Yield=71%).
Mp=190° C.
Thin layer chromatography: Rf=0.3 (ethyl acetate)

EXAMPLE 11

1-(m-trifluoromethylphenyl) 1,4-dihydro 3-(4-methylpiperazino) 4-oxo 6-methyl pyridazine (Compound 10)

1.47 g of chlorinated compound 9 are treated for 2¼ hours at 100° C. with 7.35 ml of N-methyl piperazine. After return to room temperature, the excess amine is evaporated in vacuum. The residual oil is taken up by a solution of sodium bicarbonate and extracted with ethyl acetate. The organic phase, washed with water and then in salt water, is dried and then concentrated under vacuum.

By trituration in petroleum ether and recrystallization from ethyl ether, compound 10 is obtained (1.35 g)
(Yield=77%)
MP=130° C.
Thin layer chromatography: Rf=0.63 ($CHCl_3$—MeOH: 50—50).

EXAMPLE 12

1-(m-trifluoromethylphenyl) 1,4-dihydro 3-(beta-aminoethylamino) 4-oxo 6-methyl pyridazine (Compound 11)

The chlorinated derivative 9 (1 g) in ethylene diamine (5 ml) is brought to 80° C. for 2 hours. After evaporation of the ethylene diamine, it is taken up in salt water and extracted with ethyl acetate.

The organic phase, dried over $Na_2SO_4$, is concentrated in vacuum and the residue obtained is chromatographed on a silica column (elution $CHCl_3$—MEOH—$NH_4OH$:90:9:1). Compound 11 is thus obtained (0.86 g)

(Yield=81%)
MP=130° C.
Thin layer chromatography: Rf=0.15
(CHCl₃—MeOH—NH₄OH:90:9:1)

EXAMPLES 1-42

The following table summarizes the main products synthesized which illustrate the invention without limiting its scope.

| N° | $R_1$ | $R_2$ | $R_3$ | $R_4$ | $R_5$ | MP °C. |
|---|---|---|---|---|---|---|
| 1 | mCF₃ | H | CH₃ | H | H | 179° C. |
| 2 | mCF₃ | H | CH₃ | H | COOtBu | 170–171° C. |
| 3 | mCF₃ | H | H | H | H | 131° C. |
| 4 | mCF₃ | H | CH₃ | H | CONHBu | 157° C. |
| 5 | mCF₃ | H | CH₃ | H | CO-C₆H₅ | 186° C. |
| 6 | mCF₃ | H | CH₃ | H | CH₃ | 179° C. |
| 7 | mCF₃ | H | CH₃ | CH₃ | CH₃ | 150° C. |
| 8 | pCl | H | CH₃ | H | CH₃ | 214–215° C. |
| 10 | mCF₃ | H | CH₃ | | N-methylpiperidinyl | 130° C. |
| 11 | mCF₃ | H | CH₃ | H | CH₂CH₂NH₂ | 130° C. |
| 12 | pOCH₃ | H | CH₃ | H | H | 220° C. |
| 13 | O.Cl | H | CH₃ | H | H | 215° C. |
| 14 | m.Cl | H | CH₃ | H | H | 219° C. |
| 15 | O.CF₃ | H | CH₃ | H | H | 236° C. |
| 16 | mCF₃ | H | CH₃ | H | COOEt | 192° C. |
| 17 | mCF₃ | H | CH₃ | H | COOCH₂-C₆H₅ | 151° C. |
| 18 | mCF₃ | H | CH₃ | H | COCH₃ | 191° C. |
| 19 | mCF₃ | H | CH₃ | H | COCH₂NH-cyclopropyl | 220° C. |
| 20 | mCF₃ | H | CH₃ | H | CH₂CH₂-N-morpholinyl | 101° C. |
| 21 | mCF₃ | H | | H | H | 150° C. |
| 22 | H | H | CH₃ | H | CH₃ | 191° C. |
| 23 | 2.Cl | 5-CF₃ | CH₃ | H | H | 107° C. |
| 24 | 2.Cl | 5-CF₃ | H | H | H | 140° C. |
| 25 | mCF₃ | H | Et | H | H | 174° C. |
| 26 | H | H | CH₃ | H | Et | 185° C. |
| 27 | mCF₃ | H | H | H | CH₃ | 126° C. |
| 28 | 2.Cl | 5-Cl | CH₃ | H | H | 199° C. |
| 29 | 2.Cl | 6-Cl | CH₃ | H | H | 227° C. |
| 30 | 2.Cl | 5-CF₃ | H | H | CH₃ | 167° C. |
| 31 | mCF₃ | H | CH₃ | H | CON-piperazinyl-pyrimidine | 163° C. |
| 32 | mCF₃ | H | CH₃ | H | C(=O)-N-morpholinyl | 236° C. |

-continued

| N° | R₁ | R₂ | R₃ | R₄ | R₅ | MP °C. |
|---|---|---|---|---|---|---|
| 33 | mCF₃ | H | CH₃ | H | 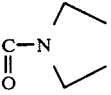 | 139° C. |
| 34 | mCF₃ | H | CH₃ | H | CONH₂ | 255° C. |
| 35 | mCF₃ | H | H | CH₃ | CH₃ | 130° C. |
| 36 | mCF₃ | H | CH₃ | | 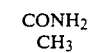 | 111° C. |
| 37 | mCF₃ | H | CH₃ | | 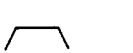 | 134° C. |
| 38 | mCF₃ | H | CH₃ | | 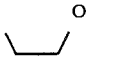 | 118° C. |
| 39 | mCF₃ | H | CH₃ | | 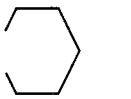 N—CH₂-phenyl | 128° C. |
| 40 | mCF₃ | H | CH₃ | | 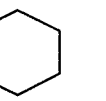 N-phenyl | 168° C. |
| 41 | mCF₃ | H | CH₃ | H | COO-phenyl | 145° C. |
| 42 | mCF₃ | H | CH₃ | | 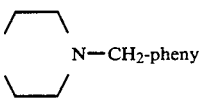 | 175° C. |

EXPERIMENTAL

Various toxicological and pharmacological tests were carried out on the compounds forming the object of the present invention.

A—TOXICOLOGY

The compounds of the invention were subjected to toxicity tests. Toxicity was determined by the 50% lethal dose (LD 50). It was determined on lots of 10 mice orally and calculated in accordance with the method of Thomson and Weil (Biometrics, 1958, 8, 249).

The LD 50 of the compounds tested is greater than 500 mg/kg by mouth.

B—PHARMACOLOGICAL PROPERTIES

The pharmacological experiments made it possible to show remarkable properties on the central nervous system and more particularly anxiolytic properties.

The anxiolytic activity of the compounds of the present invention was shown by the Vogel test (THIEBOT M. H. et al., Eur. J. Pharm. 88, p 111-116, 1983).

The results obtained on certain products of the present invention, are set forth below:

| PRODUCT | 30 mg/kg p.o. % increase/control |
|---|---|
| 1 | 107% |
| 6 | 64% |
| 7 | 59% |
| 16 | 75% |
| 23 | 141% |
| 24 | 128% |
| 27 | 132% |

2) THERAPEUTIC APPLICATIONS

Based on their pharmacological properties, the compounds of the present invention can be used in human therapy for the treatment of various mental diseases or disturbances of the central nervous system, particularly anxiety, by the administration to a subject in need thereof an amount of such compound which is effective for such purpose by any one of the usual routes of administration.

Pharmaceutical preparations containing an effective amount of these active principles can be used, if desired, and may be presented in a form for oral, rectal, or parenteral administration, for instance capsules, tablets, gels and solutions in which they are associated with suitable pharmaceutically-acceptable excipients, carriers, or diluents.

It is also possible to combine other pharmaceutically and therapeutically acceptable active principles therewith.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

We claim:

1. An Aryl pyridazine compound of formula I

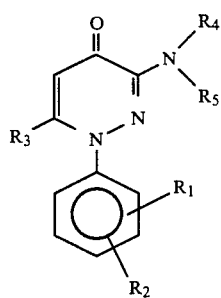

in which:

$R_1$, $R_2$, which are identical or different, represent a lower alkyloxy group, a halogen, or a trifluoromethyl radical;

$R_3$ represents a hydrogen, a lower-alkyl group, whether or not branched, a phenyl or phenyl lower-alkyl group, $R_4$ represents hydrogen, a linear or branched lower-alkyl or lower-cycloalkyl radical or a radical which forms with $R_5$ and the nitrogen atom to which they are bound a heterocycle selected from pyrrole, pyrrolidine, morpholine, piperidine, imidazole, piperazine, 4-methylpiperazine, and 4-phenylpiperazine;

$R_5$ represents:

hydrogen, a linear or branched lower-alkyl radical, an aminoalkyl group II

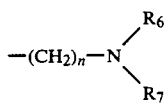

in which n is 2 to 5, inclusive, and $R_6$, $R_7$, which are identical or different, represent hydrogen, a lower-alkyl or cycloalkyl group or, together with the nitrogen atom to which they bound, form a heterocycle selected from piperidine, pyrrolidine, morpholine or piperazine, 4-methylpiperazine, 4-pyrimidinylpiperazine, and 4-phenylpiperazine:

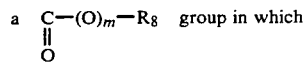

m is to 0 or 1 and $R_8$ represents a lower-alkyl group, linear or branched, phenyl or phenyl lower-alkyl group, or an amino alkyl group II as defined above;

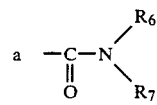

group in which $R_6$ and $R_7$ have the same meanings as above; "lower" always meaning at most $C_6$, or a therapeutically-acceptable organic or inorganic salt thereof.

2. A compound of claim 1, selected from the group consisting of:

1-(m-trifluoromethylphenyl) 1,4-dihydro 4-oxo 3-amino 6-methyl pyridazine 1-(m-trifluoromethylphenyl) 1,4-dihydro 3-(t-butoxycarbonylamino) 4-oxo 6-methyl pyridazine 1-(m-trifluoromethylphenyl) 1,4-dihydro 4-oxo 3-amino pyridazine 1-(m-trifluoromethylphenyl) 1,4-dihydro 3-(3'-n-butylureido 4-oxo 6-methyl pyridazine 1-(m-trifluoromethylphenyl) 1,4-dihydro 3-benzamido 4-oxo 6-methyl pyridazine 1-(m-trifluoromethylphenyl) 1,4-dihydro 3-methylamino 4-oxo 6-methyl pyridazine 1-(m-trifluoromethylphenyl) 1,4-dihydro 3-dimethylamino 4-oxo 6-methyl pyridazine 1-(p-chlorophenyl) 1,4-dihydro 3-methylamino 4-oxo 6-methyl pyridazine 1-(m-trifluoromethylphenyl) 1,4-dihydro 3-(4 methyl piperazino) 4-oxo 6-methyl pyridazine 1-(m-trifluoromethylphenyl) 1,4-dihydro 3-(beta-aminoethylamino) 4-oxo 6-methyl pyridazine 1-(p-methoxyphenyl) 1,4-dihydro 4-oxo 3-amino 6-methyl pyridazine 1-(o-chlorophenyl) 1,4-dihydro 4-oxo 3-amino 6-methyl pyridazine 1-(m-chlorophenyl) 1,4-dihydro 4-oxo 3-amino 6-methyl pyridazine 1-(o-trifluoromethylphenyl) 1,4-dihydro 4-oxo 3-amino 6-methyl pyridazine 1-(m-trifluoromethylphenyl) 1,4-dihydro 4-oxo 6-methyl pyridazine- 3-ethyl carbamate 1-(m-trifluoromethylphenyl) 1,4-dihydro 4-oxo 6-methyl pyridazine-3-benzyl carbamate 1-(m-trifluoromethylphenyl) 1,4-dihydro 3-acetamido 4-oxo 6-methyl pyridazine 1-(m-trifluoromethylphenyl) 1,4-dihydro 3-cyclopropyl glycinamido 4-oxo 6-methyl pyridazine 1-(m-trifluoromethylphenyl) 1,4-dihydro 3-(beta-morpholino ethylamino 4-oxo 6 methyl pyridazine 1-(m-trifluoromethylphenyl) 1,4-dihydro 3-amino 4-oxo 6-phenyl pyridazine 1-(2-chloro 5-trifluoromethylphenyl) 1,4-dihydro 3-amino 4-oxo 6-methyl pyridazine 1-(2-chloro 5-trifluoromethylphenyl) 1,4-dihydro 3-amino 4-oxo pyridazine 1-(m-trifluoromethylphenyl) 1,4-dihydro 3-amino 4-oxo 6-ethyl pyridazine 1-(m-trifluoromethylphenyl) 1,4-dihydro 3-methylamino 4-oxo pyridazine 1-(2,5-dichlorophenyl) 1,4-dihydro 3-amino 4-oxo 6-methyl pyridazine 1-(2,6-dichlorophenyl) 1,4-dihydro 3-amino 4-oxo 6-methyl pyridazine 1-(2-chloro 5-trifluoromethylphenyl) 1,4-dihydro 3-methylamino 4-oxo pyridazine 1-(m-trifluoromethylphenyl) 1,4-dihydro 4-oxo 6-methyl 3-[4'-(2''-pyrimidinyl)piperazinocarbonylamino] pyridazine 1-(m-trifluoromethylphenyl) 1,4-dihydro 4-oxo 3-(3'3' diethyl)ureido 6-methyl pyridazine 1-(m-trifluoromethylphenyl) 1,4-dihydro 3-ureido 4-oxo 6-methyl pyridazine 1-(m-trifluoromethylphenyl) 1,4-dihydro 3-dimethylamino 4-oxo pyridazine 1-(m-trifluoromethylphenyl) 1,4-dihydro 3-morpholino 4-oxo 6-methyl pyridazine 1-(m-trifluoromethylphenyl) 1,4-dihydro 3-piperidino 4-oxo 6-methyl pyridazine 1-(m-trifluoromethylphenyl) 1,4-dihydro 3-pyrrolidino 4-oxo 6-methyl pyridazine 1-(m-trifluoromethylphenyl) 1,4-dihydro 3-(4-benzyl-1-piperazinyl 4-oxo 6-methyl pyridazine 1-(m-trifluoromethylphenyl) 1,4-dihydro 3-(4-phenyl-1-piperazinyl) 4-oxo 6-methyl pyridazine 1-(m-trifluoromethylphenyl) 1,4-dihydro 4-oxo 6-methyl pyridazine-3-phenyl carbamate 1-(m-trifluoromethylphenyl) 1,4-dihydro 3-pyrrolo 4-oxo 6-methyl pyridazine and pharmaceutically-acceptable salts thereof.

3. A pharmaceutical composition useful in the treatment of anxiety which contains as active principle an effective anxiolytic amount of a compound of claim 1 in association with a pharmaceutically-acceptable carrier or diluent.

4. A method of treating anxiety in a subject in need thereof, comprising the step of administering an amount of a compound of claim 1 which is effective for said purpose.

5. Method of claim 4 wherein the compound is a compound as defined in claim 2.

6. A pharmaceutical composition of claim 3 wherein the active ingredient is a compound as defined in claim 2.

7. A method of treating anxiety in a subject in need thereof, comprising the step of administering an effective anxiolytic amount of an aryl pyridazine compound of formula I

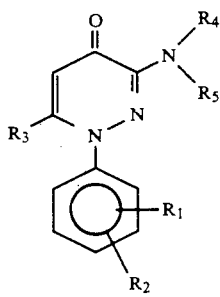 (I)

in which:

$R_1$ and $R_2$, which are identical or different, represent hydrogen, a lower-alkyl group or a lower-alkyloxy group, a halogen, or a trifluoromethyl radical;

$R_3$ represents hydrogen, a lower-alkyl group, whether or not branched, a phenyl, or a phenyl lower-alkyl group, $R_4$ represents hydrogen, a linear or branched lower-alkyl or lower-cycloalkyl radical, or a radical which forms with $R_5$ and the nitrogen atom to which they are bound a heterocycle selected from pyrrole, pyrrolidine, morpholine, piperidine, imidazole, piperazine, 4-methylpiperazine, and 4-phenylpiperazine, $R_5$ represents:

hydrogen, a linear or branched lower-alkyl radical, an aminoalkyl group II

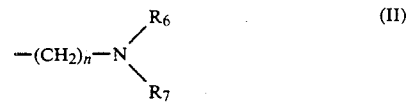 (II)

in which n is 2 to 5, inclusive, and $R_6$, $R_7$, which are identical or different, represent hydrogen, a lower-alkyl or cycloalkyl group or, together with the nitrogen atom to which they bound, form a heterocycle selected from piperidine, pyrrolidine, morpholine, piperazine, 4-methylpiperazine, 4-pyrimidinylpiperazine, and 4-phenylpiperazine,

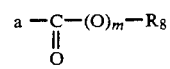

group in which ms is 0 or 1 and $R_8$ represents a lower-alkyl group, linear or branched, a phenyl or a phenyl lower-alkyl group, or an aminoalkyl group II as defined above;

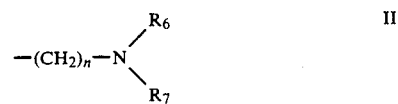 II group in which $R_6$ and $R_7$ have the same meanings as above; the term "lower" always meaning at most $C_6$, or a therapeutically-acceptable organic or inorganic salt thereof.

8. A method of claim 7, wherein the compound is 1-phenyl 1,4-dihydro 3-methylamino 4-oxo 6-methyl pyridazine.

9. A method of claim 7, wherein the compound is 1-phenyl 1,4-dihydro 3-ethylamino 4-oxo 6-methyl pyridazine.

* * * * *

UNITED STATES PATENT AND TRADEMARK OFFICE
CERTIFICATE OF CORRECTION

PATENT NO. : 5,059,599

DATED : Oct. 22, 1991

INVENTOR(S) : Gilbert Mouzin, Henri Cousse, Jean-Francois Patoiseau, Jean-Marie Autin, Dennis Bigg It is certified that error appears in the above-identified patent and that said Letters Patent is hereby corrected as shown below:

Column 3, approximately line 39; "compound followed" should read -- compound, followed --.
Column 5, line 9; "Yield--71%)." should read -- (Yield-(d-71%).
Column 6, line 8; "6 methyl" should read -- 6-methyl --.
Column 6, line 55; "2¼" should read -- 2½ --.
Column 7, approximately line 4; "4oxo" should read -- 4-oxo --.
Column 7, approximately line 31; "95 ethanol" should read -- 95° ethanol --.
Column 8, approximately line 40; "2¼ should read -- 2½ --.
Column 8, line 67; "MEOH" should read -- MeOH --.
Column 13, line 66; "m is to 0" should read -- m is 0 --.

Column 16, line 36; "ms is" should read -- m is --.
  3-26-91, pg. 5, ln. 1 - old Cl. 8)
Column 16, approximately line 41-43;

reads " $-(CH_2)_n-N\begin{smallmatrix}R_6\\R_7\end{smallmatrix}$ II " should read " a $-\underset{\underset{O}{\|}}{C}-N\begin{smallmatrix}R_6\\R_7\end{smallmatrix}$ --"

Signed and Sealed this

Ninth Day of March, 1993

*Attest:*

STEPHEN G. KUNIN

*Attesting Officer*   *Acting Commissioner of Patents and Trademarks*

UNITED STATES PATENT AND TRADEMARK OFFICE
CERTIFICATE OF CORRECTION

PATENT NO. : 5,059,599

DATED : Oct. 22, 1991

INVENTOR(S) : Gilbert Mouzin, Henri Cousse, Jean-Francois Patoiseau, Jean-Marie Autin, Dennis Bigg It is certified that error appears in the above-identified patent and that said Letters Patent is hereby corrected as shown below:

Column 3, approximately line 39; "compound followed" should read -- compound, followed --.

Column 5, line 9, "Yield--71%)." should read --(Yield--71%).--.

Column 6, line 8; "6 methyl" should read -- 6-methyl --.

Column 6, line 55; "2¼" should read -- 2½ --.

Column 7, approximately line 4; "4oxo" should read -- 4-oxo --.

Column 7, approximately line 31; "95 ethanol" should read -- 95° ethanol --.

Column 8, approximately line 40; "2¼ should read -- 2½ --.

Column 8, line 67; "MEOH" should read -- MeOH --.

Column 13, line 66; "m is to 0" should read -- m is 0 --.

Column 16, line 36; "ms is" should read -- m is --.

UNITED STATES PATENT AND TRADEMARK OFFICE
CERTIFICATE OF CORRECTION

PATENT NO. : 5,059,599
DATED : Oct. 22, 1991
INVENTOR(S) : Gilbert Mouzin, Henri Cousse, Jean-Francois Patoiseau, Jean-Marie Autin, Dennis Bigg It is certified that error appears in the above-indentified patent and that said Letters Patent is hereby corrected as shown below:

Column 16, approximately line 41-43;

reads  II should read a $-\underset{\underset{O}{\|}}{C}-N\underset{R_7}{\overset{R_6}{\diagup}}$ This Certificate supersedes Certificate of Correction issued March 9, 1993.

Signed and Sealed this

Ninth Day of November, 1993

Attest:

BRUCE LEHMAN

Attesting Officer      Commissioner of Patents and Trademarks